United States Patent [19]

Berube

[11] Patent Number: 4,946,794

[45] Date of Patent: Aug. 7, 1990

[54] VISUALIZATION OF PROTEINS ON ELECTROPHORESIS GELS USING PLANAR DYES

[75] Inventor: Gene R. Berube, Cheshire, Conn.

[73] Assignee: Protein Databases, Inc., Huntington Station, N.Y.

[21] Appl. No.: 132,978

[22] Filed: Dec. 15, 1987

Related U.S. Application Data

[63] Continuation of Ser. No. 943,623, Dec. 18, 1986, abandoned, which is a continuation of Ser. No. 765,969, Aug. 15, 1985, abandoned.

[51] Int. Cl.$^5$ .................. G01N 21/78; G01N 33/68
[52] U.S. Cl. ................................ 436/86; 436/169; 436/174; 436/177
[58] Field of Search ............... 436/86, 87, 88, 71, 436/164, 169, 174–177; 422/61

[56] References Cited

U.S. PATENT DOCUMENTS

| | | |
|---|---|---|
| 3,201,202 | 8/1965 | Searcy et al. ............... 436/87 X |
| 4,023,933 | 5/1977 | Bradford et al. ............ 436/87 |
| 4,219,337 | 8/1980 | Grossberg et al. .......... 436/86 |
| 4,239,495 | 12/1980 | Girdler et al. ............... 436/86 |
| 4,405,720 | 9/1983 | Merril ......................... 436/86 |
| 4,434,234 | 2/1984 | Adams et al. ................ 422/61 |
| 4,495,279 | 1/1985 | Karpetsky et al. .......... 436/86 X |
| 4,555,490 | 11/1985 | Merril ......................... 436/86 |
| 4,575,452 | 3/1986 | Lee et al. ..................... 422/61 |

FOREIGN PATENT DOCUMENTS

0099260  6/1984  Japan .................. 436/169

OTHER PUBLICATIONS

Davis, Ann. N.Y. Acad. Sci., vol. 121, pp. 404–427, 1964.
Gorovsky et al, Anal. Biochem., vol. 35, pp. 359–370, 1970.
Merril et al, Proc. Natl. Acad. Sci. U.S.A., vol. 76, pp. 4334–4339, 1979.
Dzandu et al, Proc. Natl. Acad. Sci. U.S.A., vol. 81, pp. 1733–1737, 1984.
Merril et al, Anal. Biochem., vol. 110, No. 1, pp. 201–207, 1981.
Goldman et al, Clin. Chem., vol. 26, No. 9, pp. 1317–1322, 1980.
Fazekas de St. Groth et al, Biochem. Biophys. Acta, vol. 71, pp. 377–391, 1963.
Meyer et al, Biochem. Biophys. Acta, vol. 107, pp. 144–145, 1965.
Fairbanks et al, Biochemistry, vol. 10, pp. 2606–2617, 1971.

*Primary Examiner*—Robert J. Hill, Jr.
*Attorney, Agent, or Firm*—Morgan & Finnegan

[57] ABSTRACT

A rapid, self limiting, sensitive and reproducible method of visualization of proteins which have been separated by gel electrophoresis is disclosed.

6 Claims, No Drawings

VISUALIZATION OF PROTEINS ON ELECTROPHORESIS GELS USING PLANAR DYES

This is a continuation of co-pending application Ser. No. 943,623 filed Dec. 18, 1986 now abandoned, which in turn is a continuation of application Ser. No. 765,969, filed Aug. 15, 1985, now abandoned.

BACKGROUND OF THE INVENTION

This invention relates to a reproducible method for visualizing proteins which have been separated by gel electrophoresis. More particularly, it relates to a method which involves the steps of fixing, staining and exposure to a metal complexing agent of an electrophoresed gel in order to produce a highly sensitive negative stain.

The employment of one and two dimensional gel electrophoretic separations of proteins have made possible the analysis of complex biological processes. A prevailing and predominant problem associated with the aforesaid analysis is the absence of a rapid, self limiting, sensitive, and reproducible method for visualizing the separated proteins.

Various methods referenced hereinafter suffer from one or more deficiencies in these parameters.

1. Fazekas de St. Groth, S.; Webster, R. G.; and Datyner, A. (1963). New staining procedures for quantitative estimation of proteins on electrophoretic strips. Biochem. Biophys. Acta 71:377-391—an early paper which describes the use of Coomassie Brilliant Blue R250 and Procion Brilliant Blue RS in staining proteins separated by cellulose acetate strip electrophoresis.

2. Meyer, T. S. and Lamberts, B. L. (1965) Use of Coomassie Brilliant Blue R250 for the electrophoresis of microgram quantities of parotid saliva proteins on acrylamide gel strips. Biochem. Biophys. Acta 107:144-145—an early paper which describes the use of Coomasie Brilliant Blue R250 to stain acrylamide gels.

3. Davis, B. J. (1964) Disc electrophoresis-II. Method and application to human serum proteins. Ann. N.Y. Acad. Sci. 121:404-427—a paper commonly referred to for Amido Schwartz (Napthol Blue Black, C.I. 20470) staining of proteins in acrylamide gels.

4. Gorovsky, M. A.; Carlson, K. and Rosenbaum, J. L. (1970) Simple method for quantitative densitometry of polyacrylamide gels using Fast Green. Anal. Biochem. 35:359-370—an early paper which describes the use of Fast Green to stain proteins in acrylamide gels. The staining responses of proteins is the most linear with respect to protein concentration.

5. Merril, C. R.; Switzer, R. C.; and Van Keuren, M. L. (1979) Trace polypeptides in cellular extracts and human body fluids detected by two-dimensional electrophoresis and a highly sensitive silver stain. Proc. Natl. Acad. Sci. USA 76:4334-4339—an early paper which describes highly sensitive silver stain for proteins on acrylamide gels; currently the most sensitive method to detect 'cold' protein.

6. Dzandu, J. K.; Deh, M. E.; Barratt, D. L.; and Wise, G. E. (1984) Detection of erythrocyte membrane proteins, sialoglycoproteins, and lipids in the same polyacrylamide gel using a double-stain technique. Proc. Natl. Acad. Sci. USA 81:1733-1737—this paper describes a double stain technique to visualize sialoglycoproteins and lipid in polyacrylamide gels.

7. Fairbanks, G.; Steck, T. L.; and Wallach, D. F. H. (1971) Electrophoretic analysis of the major polypeptides of the human erythrocyte membrane. Biochemistry 10:2606-2617—an early paper which describes the use of periodic acid-Schiff reagent (PAS) to stain glycoproteins in acrylamide gels.

Currently, sensitive work is accomplished with the aid of radiolabeled aminoacids. Since radiolabeled amino acids cannot be used for all types of sensitive work, e.g., sensitive work involving human tissue or proteins lacking the particular amino acid, it is highly desirable to have a staining technique which provides a highly sensitive negative stain. Until now, the most sensitive staining method to date was generally considered to be the silver stain. This method, however, entails substantial amounts of time and considerable care to perform.

The staining procedure herein disclosed and claimed relies on the use of planar dyes in combination with a complexing metal salt to differentiate between the matrix and the protein containing spot.

SUMMARY OF THE INVENTION

In accordance with this invention, there is disclosed and claimed a method for the analysis of proteins separated by gel electrophoresis which comprises the steps of fixing the electrcphoresed gel, staining the electrophoresed gel with a planar dye component, and exposing the electrophoresed gel to a metal complexing agent, the resulting method producing a highly sensitive negative stain wherein the gel is markedly stained in comparison to the transparent separated proteins.

In a preferred embodiment, two of the fixing, staining and exposing steps are effected simultaneously; however, it is possible to carry out these three steps in sequential manner.

In another preferred embodiment, the gel used for electrophoresis is an acrylamide polymer such as polyacrylamide. However, other gel matrices can be treated in accordance with the present method, for example, cellulosic polymers such as cellulose acetate, nitrocellulose, etc.

The planar dye component comprises any planar dye which, because of its planar configuration, is precluded from penetrating the protein components to any significant degree. Typical examples include acridine orange, rhodamine, eosin, fluorescein and Coomassie brilliant blue.

In another preferred embodiment of this invention, the metal complexing agent which complexes with the aforesaid planar dye is selected from chromium, silver, magnesium and calcium salts.

The present invention also contemplates kits useful for visualization of proteins separated on polyacrylamide electrophoresis gels which comprises as a first reagent, an aqueous mixture containing fixing agent and a planar dye component selected from acridine orange, rhodamine, eosin, fluorescein or Coomassie brilliant blue; and, as a second reagent, a metal complexing agent capable of complexing with said planar dye is selected from chromium, silver, magnesium or calcium salts.

A similar kit which comprises, as a first reagent, an aqueous mixture containing fixing agent and a metal complexing agent selected from chromium, silver, magnesium or calcium salts; and, as a second reagent, a planar dye component selected from acridine orange, rhodamine, eosin, fluorescein or Coomassie brilliant blue is also contemplated by the present invention.

DETAILED DESCRIPTION OF THE INVENTION

The present invention provides a rapid, self-limiting, sensitive, and reproducible method for visualization of proteins which have been separated using one or two dimensional gel electrophoresis. Such a method is essential to accelerate the pace of research in identifying and quantifying problems.

The procedures associated with one or two dimensional gel electrophoresis are well-known and documented in the literature—see for instance:

1. O'Farrell, P. H. (1975) High resolution two-dimensional electrophoresis of proteins. J. Biol. Chem. 250, 4007–4021.
2. Garrels, J. I. (1979) Two-dimensional gel electrophoresis and computer analysis of proteins synthesized by clonal gel lines. J. Biol. Chem. 254, 7961–7977.
3. Garrels, J. I. (1983) Quantitative two-dimensional gel electrophoresis of proteins. Meth. Enzym. 100, 411–423.
4. Garrels, J. I., Farrar, J. T., and Burwell, C. B. (1984) The QUEST system for computer-analyzed two-dimensional electrophoresis of proteins. In: Two-dimensional gel electrophoresis of proteins. Eds. Celis, J. E. and Bravo, R. Academic Press, New York, pp. 37–91.

The term "protein" as used herein means a high molecular weight polypeptide of L-amino acids usually produced by living cells. It will also include conjugated protein in which there may be a nonprotein portion such as a glyceride, phospholipid, cholesterol, etc.

After the proteins in a sample are separated by a gel electrophoresis technique, the electrophoresed gel is subjected to the method of this invention, wherein, in a preferred embodiment, an electrophoresed acrylamide gel containing a number of separated proteins is first subjected to a fixing and staining step and then to an exposing step in which a planar dye component used in the staining step complexes with a metal salt to differentiate between the acrylamide matrix and the protein-containing spots.

The staining procedure described herein can be carried out effectively in either of two modes:
- the metal salt is included in the fixing bath and staining is conducted post fixation
- the stain (planar dye) is incorporated into the fixing bath and the metal salt added post fixation.

The unusual and unexpected character of the planar dye component to provide significantly enhanced differentiation between the matrix and protein is shown by the following comparative example. Two related dye materials Rhodamine B,O and Malachite Green, oxalate, were used as the stain during the staining step. The result of this comparison as carried out by the procedures set forth in the examples which follow, shows the planar dye to produce a sensitive negative stain whereas the non-planar dye produced only a very weak positive stain.

Planar dyes used in the present invention complex with a metal salt surrounding proteinaceous material to differentiate between the acrylamide matrix and the proteinaceous material, but not to the proteinaceous material itself. The planar dyes useful in the invention are sterically hindered from attaching to the protein due to various factors such as the density of the protein-metal complex, and instead attach to the metal surrounding the protein. Examples I-V of the subject application illustrate the resulting negative stain obtained by following the procedure of the invention.

Exemplary of suitable planar dyes include acridine orange, rhodamine, eosin, fluorescein or Coomassie brilliant blue.

Fixation, as used herein, means a fixing in a gel matrix effected by any of several accepted methods for fixing acrylmmide gels such as acetic acid/methanol, trichloroacetic acid/methanol, formaldehyde/methanol, etc. Fixation can be achieved in periods as short as about 1 hour and as long as several days, usually with similar results.

The metal salt used herein to complex with the planar dye is typically a chromate salt such as potassium dichromate or barium chromate; however, other suitable metal salts include magnesium and calcium salts such as magnesium chloride and calcium chloride. The suitability of any metal salt for use herein is restricted only in the sense that the metal must complex with the planar dye to produce a visible color. The result is new and unexpected in that the complexation between metal salt and planar dye produces a highly sensitive negative stain.

EXAMPLE I

A two-dimensional electrophoresed acrylamide gel used to separate two known proteins phosphorylase B and ovalbumin was subjected to the following treatment.

A. FIXATION—The electrophoresed gel was inserted into a bath containing the following ingredients:

| | |
|---|---|
| Acetic acid | 100 ml. |
| Methanol | 500 ml. |
| 5% Rhodamine B,O C.I. 45170 | 100 ml. |
| Distilled water | 300 ml. | for approximately 1 hour at room temperature.

B. After a water rinse, the fixed gel was exposed to a chromium salt mixture containing the following:

| | |
|---|---|
| Potassium dichromate | 1 g. |
| Acetic acid (glacial) | 10 ml. |
| Water | 90 ml. | by insertion therein for about 15 min. at room temperature. After drying, the gel upon visual inspection shows a highly negative stain—the gel matrix stains to a semiopaque purple whereas the protein spots are transparent.

EXAMPLE II

The procedure of Example I is repeated except that the following dyes are used in lieu of rhodamine:
Acridine orange C.I. 46005
Eosin B C.I. 45400
Fluorescein
Coomassie Brilliant Blue R250
to provide similar sensitive negative stains.

EXAMPLE III

The procedure of Example I is repeated except that in lieu of potassium dichromate, the following metal complexing salts in equivalent amounts are used with comparable results:
barium chromate magnesium chloride
calcium chloride

EXAMPLE IV

The procedure of Example I is repeated with comparable results wherein the following Fixing (A) and Exposing (B) compositions are used instead:

| A. Acetic Acid | 100 ml. |
|---|---|
| Methanol | 500 ml. |
| Potassium dichromate | 1 g. |
| Distilled water | 300 ml. |
| B. 5% Rhodamine B,O | 100 ml. |
| Acetic acid (glacial) | 10 ml. |
| Water | 90 ml. |

EXAMPLE V

The procedure of Example I is repeated for an electrophoresed (cellulosic) matrix containing separated proteins with comparable results.

It should be understood by those skilled in the art that various modifications may be made in the present invention without departing from the spirit and scope thereof as described in the specification and defined in the appended claims.

What is claimed is:

1. A method for analyzing proteins comprising separating proteins contained in a gel by electrophoresis to produce an electrophoresed gel, fixing the separated proteins on the electrophoresed gel, exposing the electrophoresed gel to a planar dye component selected from the group consisting of acridine orange, rhodamine, eosin and fluorescein, which is precluded from penetrating the proteins, and exposing the electrophoresed gel to a metal salt selected from the group consisting of chromium, silver, magnesium and calcium salts capable of complexing with said planar dye component to produce a color, thereby producing a highly sensitive negative stain wherein the gel is markedly stained in comparison to the separated proteins which are not stained.

2. The method of claim 1 wherein the proteins are separated using one or two dimensional gel electrophoresis.

3. The method of claim 1 wherein the gel is derived from an acrylamide or cellulosic polymer.

4. The method of claim 3 wherein said gel is a polyacrylamide gel.

5. The method of claim 1 wherein said metal salt is a chromate salt.

6. A method of claim 1 wherein proteins are separated two dimensionally on a polyacrylamido gel, the planar dye component is rhodamine, and the metal salt is potassium dichromate.

* * * * *